United States Patent [19]

Bernauer et al.

[11] 4,317,914
[45] Mar. 2, 1982

[54] OXAZOLINES

[75] Inventors: Karl Bernauer, Oberwil; Karlheinz Pfoertner, Basel, both of Switzerland

[73] Assignee: Hoffmann-La Roche Inc., Nutley, N.J.

[21] Appl. No.: 215,965

[22] Filed: Dec. 12, 1980

[30] Foreign Application Priority Data

Dec. 21, 1979 [CH] Switzerland ............... 11410/79
Oct. 21, 1980 [CH] Switzerland ............... 7856/80

[51] Int. Cl.$^3$ ............... C07D 263/10; A61K 31/42
[52] U.S. Cl. ............... 548/239; 260/239 A; 204/158 R; 424/272; 564/305
[58] Field of Search ............... 548/239

[56] References Cited

PUBLICATIONS

H. Giezendanner et al., Helv. Chim. Acta, vol. 56, p. 2611, (1973).
H. Giezendanner et al., Helv. Chim. Acta, vol. 55, p. 245, (1972).

*Primary Examiner*—Donald G. Daus
*Assistant Examiner*—Sharon A. Gibson
*Attorney, Agent, or Firm*—Jon S. Saxe; Bernard S. Leon; William G. Isgro

[57] ABSTRACT

Compounds of the formula

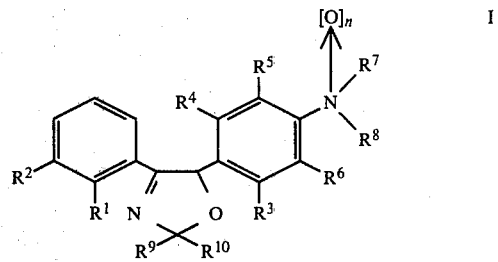

wherein
$R^1$ and $R^2$, independently, are hydrogen, halogen or lower alkyl; $R^3$, $R^4$, $R^5$, $R^6$ and $R^7$, independently, are hydrogen or $C_{1-3}$ alkyl; $R^8$ is hydrogen, lower alkyl or formyl; $R^9$ and $R^{10}$, independently, are methyl or trifluoromethyl; and n is 0 (zero) or, when both $R^7$ and $R^8$ are lower alkyl, n is 0 (zero) or 1, prepared, inter alia, from p-aminobenzaldehydes which may be N-alkyl substituted, are described. The compounds of formula I are orally active antidiabetic agents.

7 Claims, No Drawings

OXAZOLINES

BRIEF SUMMARY OF THE INVENTION

The invention relates to oxazolines of the formula

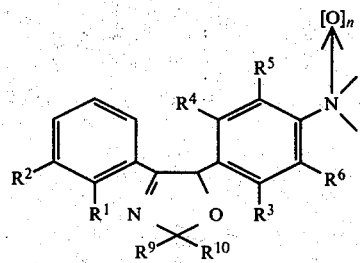

wherein $R^1$ and $R^2$, independently, are hydrogen, halogen or lower alkyl; $R^3$, $R^4$, $R^5$, $R^6$ and $R^7$, independently, are hydrogen or lower alkyl; $R^8$ is hydrogen, lower alkyl or formyl; $R^9$ and $R^{10}$, independently, are methyl or trifluoromethyl; and n is 0 or, when both $R^7$ and $R^8$ are lower alkyl, n is 0 or 1.

In another aspect, the invention relates to a process for preparing the compounds of formula I.

DETAILED DESCRIPTION OF THE INVENTION

The invention relates to oxazolines. More particularly, the invention is concerned with certain oxazolines, a process for the preparation thereof and pharmaceutical preparations containing same.

The oxazolines provided by the invention are compounds of the formula

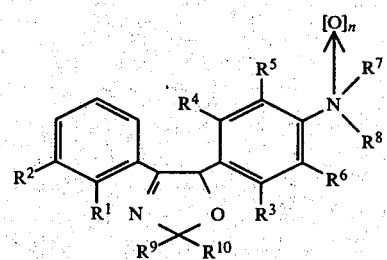

wherein $R^1$ and $R^2$, independently, are hydrogen, halogen or lower alkyl; $R^3$, $R^4$, $R^5$, $R^6$ and $R^7$, independently, are hydrogen or lower alkyl; $R^8$ is hydrogen, lower alkyl or formyl; $R^9$ and $R^{10}$, independently, are methyl or trifluoromethyl; and n is 0 or, when both $R^7$ and $R^8$ are lower alkyl, n is 0 or 1.

As used herein, the term "lower alkyl" denotes a straight-chain or branched-chain alkyl which preferably contains up to 3 carbon atoms, such as, methyl, ethyl, n-propyl and iso-propyl; methyl is especially preferred. Examples of halogen atoms are fluorine, chlorine, bromine and iodine; chlorine is preferred.

A preferred subgroup of compounds of formula I comprises those wherein each of $R^1$ to $R^6$ is hydrogen, $R^7$ is lower alkyl, and $R^8$ and n are as previously described.

Furthermore, compounds of formula I wherein each of $R^9$ and $R^{10}$ is methyl are preferred. $R^7$ preferably is hydrogen or methyl. The compounds wherein each of $R^7$ and $R^8$ is lower alkyl can be in the form of N-oxides (n=1). The non-oxidized compounds (n=0) are, however, preferred.

5-[p-(Dimethylamino)phenyl]-2,2-dimethyl-4-phenyl-3-oxazoline is an especially preferred compound of formula I.

The process provided by the invention for the preparation of the compounds of formula I hereinbefore comprises reacting a compound of the formula

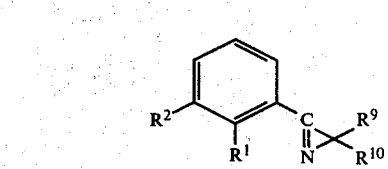

wherein $R^1$, $R^2$, $R^9$ and $R^{10}$ are as previously described, with a compound of the formula

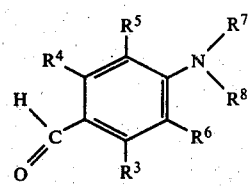

wherein $R^3$-$R^8$ are as previously described, in an inert organic solvent while irradiating with UV-light, or reacting a compound of the formula

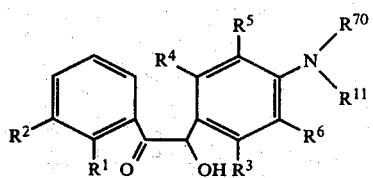

wherein
$R^1$-$R^6$ are as previously described, $R^{11}$ is hydrogen or lower alkyl, and $R^{70}$ is lower alkyl,
with acetone and ammonia, and, if desired, subjecting a thus-obtained compound of formula I wherein each of $R^7$ and $R^8$ is lower alkyl and n is 0 to N-oxidation or converting said compound by irradiation with UV-light in the presence of oxygen and a sensitizer into a compound of formula I wherein $R^8$ is formyl and, if desired, decarbonylating this compound by irradiation with UV-light of a wavelength λ greater than 300 nm.

The inert organic solvent in which the reaction of a compound of formula II with a compound of formula III is carried out is preferably an aromatic hydrocarbon, for example, benzene; an ether, for example, dioxane; or a saturated aliphatic hydrocarbon, for example, hexane or cyclohexane. The irradiation can be carried out with conventional mercury vapor lamps. The reaction solution is conveniently irradiated with UV-light of the wavelength λ greater than 300 nm and under an inert gas. In one embodiment of the process, a compound of formula I, wherein each of $R^7$ and $R^8$ is lower alkyl is irradiated in the presence of a sensitizer, for example, benzophenone and in the presence of oxygen, to yield a compound of formula I wherein $R^7$ is lower alkyl and $R^8$ is formyl. The thus-obtained N-formyl-N-alkyl compound of formula I can be decarbonylated, i.e., converted into a compound of formula I wherein $R^7$ is lower alkyl and $R^8$ is hydrogen, by irradiation with UV-light of a wavelength λ greater than 300 nm.

In the reaction of a compound of formula IV with acetone and ammonia, which leads to a compound of formula I wherein each of $R^9$ and $R^{10}$ is methyl and $R^8$ is hydrogen or lower alkyl, the ammonia is conveniently generated in situ, for example, by the action of a strong base on an ammonium salt. In a preferred embodiment, a compound of formula IV is reacted with acetone and ammonium acetate in the presence of triethylamine. The reaction can be carried out at room temperature or, preferably, while warming to a temperature not exceeding 45° C. and in the presence of a solvent, for example, an alcohol, such as, methanol.

The N-oxidation of a compound of formula I wherein n is zero can be carried out according to known methods using an oxidizing agent, for example, a peracid, such as, perbenzoic acid or m-chloroperbenzoic acid.

The solvent for the N-oxidation using a peracid is, preferably, a chlorinated hydrocarbon, such as, methylene chloride. The N-oxidation can also be carried out using acetic anhydride/hydrogen peroxide, and glacial acetic acid is conveniently used as the solvent. The N-oxidation is preferably carried out at a temperature in the range of from between 0° C. to 60° C., especially at 10°–20° C.

The compounds of formula I are useful as medicaments and can be used for the treatment of diabetes, particularly, diabetes of the elderly, that is, maturity onset diabetes. Structurally and in their mode of action the compounds of formula I have no relationship to known antidiabetics. The compounds of formula I lower the blood sugar level after repeated oral administration by increasing the peripheral glucose oxidation and/or by relieving the liver of gluconogenesis precursors. So that, in contrast to biguanidines, they bring about no rise in the blood lactate value.

The testing of the compounds of formula I in warm-blooded animals gave the following results.

TABLE 1

Activity on plasma or blood glucose after repeated oral administration
Compound: 5-[p-(Dimethylamino)-phenyl]-2,2-dimethyl-4-phenyl-3-oxazoline

| | Number of animals per group | administrations | Dosage (mg/kg) p.os | \multicolumn{5}{c}{Plasma or blood glucose (in % of blank values) after the last medication} | | | | |
|---|---|---|---|---|---|---|---|---|
| | | | | 0 | 1 | 3 | 6 | 24 hours |
| Fasted rat (1) | 6 | 5 | 88 | 76 | 76 | 78*** | — | — |
| | | 5 | 294 | — | 57** | 58*** | — | — |
| Fasted dog (2) | 3 | 5 | 29 | 82** | 75* | 77*** | 74** | 84 |
| | 3 | 5 | 88 | 77** | 75 | 78* | 76* | 74* |
| Diabetic rat (3) | | 7 | 132 | 101 | 101 | 90 | 86* | — |
| Obese-hyperglycemic mouse | | | | | | | | |
| (4) | 6 | 5 | 294 | 63* | 74 | 71 | 45*** | — |
| (5) | 12 | 11 | 44 | 83 | 77 | 84 | — | — |
| (5) | 12 | 11 | 132 | 66** | 61* | 55*** | — | — |

*p < 0.05
**p < 0.01
***p < 0.001

TABLE 2

Activity on the glycosuria in the case of intermittent subchronic oral administration to obese hyperglycemic mice Compound: 5-[p-(Dimethylamino)phenyl]-2,2-dimethyl-4-phenyl-3-oxazoline
Weekly glucose excretion in the urine (in % of blank values)

Week  1   2    3    4    5    6   7    8   9   10  11  12

Medication ⊢——⊣  ⊢——⊣   ⊢——⊣     ⊢——⊣

97  28*  6*  1*  1***  2*  2***  27*  97  9*  1*  2*

*p < 0.05
**p < 0.01
***p < 0.001

TABLE 3

Activity on the plasma in the fasted rat (1)
3 hours after the last of 5 oral medications

| Compound | Dosage [μmol/kg] 5 × p.o. | Plasma glucose (in % of the blank values) |
|---|---|---|
| A | 300 | 78*** |
| | 1000 | 58*** |
| B | 300 | 91 |
| | 1000 | 77* |
| C | 300 | 87* |
| D | 300 | 86* |
| | 1000 | 81* |

A: 5-[p-(Dimethylamino)phenyl]-2,2-dimethyl-4-phenyl-3-oxazoline
B: 5-[p-(Diethylamino)phenyl]-2,2-dimethyl-4-phenyl-3-oxazoline
C: 4'-(2,2-Dimethyl-4-phenyl-3-oxazolin-5-yl)-N-methylformanilide
D: 5-[p-(Methylamino)phenyl-2,2-dimethyl-4-phenyl-3-oxazoline The preparations containing the test compound were administered to rats and mice as a suspension in 5% gun arabic (10 ml/kg) through a stomach probe. Dogs received the preparations orally in gelatin capsules. The blank values were ascertained from animals which received only the vehicle or a blank capsule. The medication was administered daily at 9:00 a.m. and 3:00 p.m.

The plasma glucose (Tables 1 and 3) was determined according to the hexokinase method. The plasma was obtained from heparinized blood after decapitating the rats (1) or by puncturing the vena saphena (2), or there was used a filtrate, made protein-free with perchloric acid, of blood removed from the tip of the tail (3), (4), (5). The glucose in the urine was determined directly. In the case of (1), (2) and (4), the feed was withdrawn with the first of five medications.

In the case of (3), female rats received 70 mg/kg of streptozotocin subcutaneously 2 weeks before the test. In the case of (3) and (5), quantitatively controlled feed supply existed.

In the case of 5-[p-(dimethylamino)phenyl]-2,2-dimethyl-4-phenyl-3-oxazoline, the determination of the toxicity of the 10 day test in mice gave a $LD_{50}$ of 220 mg/kg and in rats a $LD_{50}$ of 970 mg/kg.

The compounds of formula I can be used for the oral treatment of diabetes in doses of 200–800 mg/day, preferably 500 mg/day, the dosage being fitted to the individual requirements of the warm-blooded animal by the physician.

The compounds of formula I can be formulated in dosage forms which are customary for oral antidiabetics, for example, tablets, dragees or capsules, which, besides the active substance, can contain adjuvant and carrier substances which are customary in such preparations.

The following Examples further illustrate the invention. All temperatures are in degrees centigrade, unless otherwise stated.

EXAMPLE 1

Preparation of 5-[p-(dimethylamino)phenyl]-2,2-dimethyl-4-phenyl-3-oxazoline 250 g of 2,2-dimethyl-3-phenyl-2H-azirine and 230 g of 4-dimethylaminobenzaldehyde were exposed to light in 5 liters of dioxane under an atmosphere of argon for 1.5 hours with a mercury high-pressure lamp of 4000 watt in a ring-mantle vessel through an interposed filter fluid. The filter fluid contained 35 g of cupric sulfate pentahydrate per liter of water and had a layer thickness of 1 cm. Not only the reaction solution but also the filter solution were cooled during the exposure to light in that they circulated with the aid of pumps through a heat-exchanger positioned outside the photoreactor. During the exposure to light the temperature of the reaction solution amounted to 35° C. measured outside the photoreactor.

Subsequently, the dioxane solution containing the reaction mixture was concentrated to 300 ml in a water-jet vacuum. This was combined with 12.5 liters of n-heptane and 7.5 liters of diethyl ether in a stirring vessel of 30 liters capacity, where the thus-diluted solution was washed four times with 8 liters of water each time. After its separation from the aqueous phase, the organic phase was dried over magnesium sulfate and, without concentration, subjected directly to column chromatography on 4 kg of aluminium oxide (neutral, activity 1). After its throughput, the column was eluted with an additional 10 liters of the same solvent mixture (6.25 liters of n-heptane and 3.75 liters of diethyl ether). The first 7 liters of solvent leaving the chromatography contained no substance at all. The following 23 liters were combined and evaporated to dryness in a water-jet vacuum, and 300 g of 5-[p-(dimethylamino)phenyl]-2,2-dimethyl-4-phenyl-3-oxazoline which was dried for 3 hours at 90° C. in a water-jet vacuum. Thereafter, the product had a melting point of 122.6° C. and was purer than 99.9% according to high-pressure liquid chromatography as well as according to differential thermal analysis.

EXAMPLE 2

Preparation of 5-[p-(diethylamino)-phenyl]-2,2-dimethyl-4-phenyl-3-oxazoline 4 g of 2,2-dimethyl-3-phenyl-2H-azirine and 5 g of 4-diethylaminobenzaldehyde were exposed to light in 350 ml of benzene at 230° C. for 4 hours under an atmosphere of argon with a mercury high-pressure lamp of 150 watt in a water-cooled ring-mantle vessel through a 3 mm thick filter of Pyrex glass. After removing the solvent in a water-jet vacuum, the residue was crystallized from n-hexane/acetone and then a second time from n-pentane/acetone. The crystalline product was then dried at 60° C. in the water-jet vacuum, and there were obtained 3,4 g of 5-[p-(diethylamino)-phenyl]-2,2-dimethyl-4-phenyl-3-oxazoline having a melting point of 104°–105° C.

EXAMPLE 3

Preparation of 5-[p-(dipropylamino)phenyl]-2,2-dimethyl-4-phenyl-3-oxazoline 10 g of 2,2-dimethyl-3-phenyl-2H-azirine and 10 g of 4-dipropylaminobenzaldehyde were exposed to light in 2 liters of benzene under an atmosphere of argon for 40 minutes with a mercury high-pressure lamp of 2000 watt in a ring-mantle vessel through an interposed filter fluid. The filter fluid contained 35 g of cupric sulfate pentahydrate per liter of water and had a layer thickness of 1 cm. Not only the reaction solution but also the filter solution were cooled during the exposure to light in that they circulated with aid of pumps through a heat-exchanger positioned outside the photoreactor. During the exposure to light the temperature of the reaction solution amounted to 26° C. measured outside the photoreactor.

After removing the solvent in a water-jet vacuum, the residue was taken up in n-hexane and crystallized at −30° C. The thus obtained 5-[p-(dipropylamino)-phenyl]-2,2-dimethyl-4-phenyl-3-oxazoline was recrystallized in the same manner. The mother liquors of the first and second crystallization were combined, and the residue obtained after evaporation was chromatographed on silica gel, the elution being carried out with dichloromethane. An additional 4 g of product were isolated in this manner. The total yield was 7.7 g; melting point 91°–92° C.

EXAMPLE 4

Preparation of 5-[p-(methylamino)phenyl]-2,2-dimethyl-4-phenyl-3-oxazoline 12 g of 2,3-dimethyl-phenyl-2H-azirine and 10 g of 4-methylaminobenzaldehyde were exposed to light in 2 liters of benzene under an atmosphere of argon with a mercury high-pressure lamp of 2000 watt in a ring-mantle vessel through an interposed filter fluid. The filter fluid contained 35 g of cupric sulfate pentahydrate per liter of water and had a layer thickness of 1 cm. Not only the reaction solution but also the filter solution were cooled during the exposure to light in that they circulated with the aid of pumps through a heat-exchanger positioned outside the photoreactor. During the exposure to light the temperature of the reaction solution amounted to 26° C. measured outside the photoreactor.

After an exposure time of 2 hours, 5 g of 2,2-dimethyl-3-phenyl-2H-azirine were again added to the reaction solution, and the mixture was exposed to light for an additional 3.5 hours.

After evaporation of the solvent in a water-jet vacuum, the residue was chromotographed twice on silica gel, the elution being carried out firstly with n-hexane/ethyl acetate (2:1) and subsequently with n-hexane/acetone (9:1). The thus-obtained product was recrystallized from n-hexane/acetone and dried at 60° C. in a water jet vacuum, and there were obtained 6 g of 5-[p-(methylamino)phenyl]-2,2-dimethyl-4-phenyl-3-oxazoline having a melting point of 138°–139° C.

EXAMPLE 5

Preparation of
4'-(2,2-dimethyl-4-phenyl-3-oxazolin-5-yl)-N-methyl-formanilide 33 g of 2,2-dimethyl-3-phenyl-2H-azirine and 26.1 g of 4-formyl-N-methylformanilide were exposed to light in 3 liters of benzene under an atmosphere of argon for 3 hours in the apparatus described in Example 4. After removing the solvent in a water-jet vacuum, the residue was dissolved in diethyl ether, and the solution was decolorized with active carbon. After filtration, the filtrate was concentrated until crystallization began. The crystallization was completed by storing the solution at 4° C. for 2 days. After suction filtration, the product was washed with cold ether and dried at 80° C. in a water-jet vacuum, and there were obtained 29.6 of 4'-(2,2-dimethyl-4-phenyl-3-oxazolin-5-yl)-N-methyl-formanilide having a melting point of 104°–105° C.

The 4-formyl-N-methylformanilide used as the starting material was prepared as follows:

60 g of N-methylformanilide were cooled to +10° C. and treated slowly while stirring with 70 g of phosphorus oxychloride. Then, the cooling source was removed, the mixture was stirred at room temperature for 3 hours, 90 g of phosphorus pentachloride were added, and the resulting mixture was stirred until the slurry, which at first became stiff, again liquified. The phosphorus oxychloride was then removed by distillation at 60° C. in a water-jet vacuum, the residue was cooled to 0° C. and neutralized with sodium hydroxide (likewise pre-cooled). The mixture was extracted with chloroform, the organic phase was dried over sodium sulfate, and the chloroform was removed by distillation. The distillation residue was chromatographed on silica gel, the elution being carried out with dichloromethane/acetone (95:5). In this manner there were obtained fractions containing 4-methylaminobenzaldehyde and 4-formyl-N-methylformanilide. The latter was recrystallized first from ether/n-hexane and then from ethanol and, after drying in a water-jet vacuum at 60° C., had a melting point of 100°–101° C.

EXAMPLE 6

Preparation of
5-[p-(methylamino)phenyl]-2,2-dimethyl-4-phenyl-3-oxazoline 5 g of 4'-(2,2-dimethyl-4-phenyl-3-oxazoline-5-yl)-N-methylformanilide were exposed to light in 2 liters of ethanol under an atmosphere of argon for 8 hours in the apparatus described in Example 4. After evaporation of the solvent in a water-jet vacuum, there remained behind an oil which was chromatographed on silica gel. The elution was carried out with dichloromethane/acetone (95:5). In order to remove accompanying impurities, the product isolated in the foregoing manner was suspended in hot petroleum ether (boiling range 80°–110° C.), removed by filtration under suction and washed on the suction filter with petroleum ether. After drying at 60° C. in a water-jet vacuum, there were obtained 2.5 g of 5-[p-(methylamino)phenyl]-2,2-dimethyl-4-phenyl-3-oxazoline having a melting point of 138°–139° C.

EXAMPLE 7

Preparation of
4'-(2,2-dimethyl-4-phenyl-3-oxazolin-5-yl-N-methylformanilide 2 g of 5-[p-(dimethylamino)phenyl]-2,2-dimethyl-4-phenyl-3-oxazoline were exposed to light in 300 ml of 1,4-dioxane in the presence of 0.5 g of benzophenone as the sensitizer with a mercury high-pressure lamp of 150 watt in a water-cooled ring-mantle vessel through a 3 mm thick filter of Pyrex glass while conducting air through the mixture for 1 hour. After removing the solvent by distillation in a water-jet vacuum, the residue was chromatographed on silica gel in order to separate the benzophenone, the elution being carried out with dichloromethane/acetone (95:5). The crude product was crystallized from diethyl ether at 4° C., and there were obtained 1.9 g of 4'-(2,2-dimethyl-4-phenyl-3-oxazolin-5-yl-N-methylformanilide having a melting point of 104°–105° C.

EXAMPLE 8

Preparation of
5-[p-(dimethylamino)phenyl]-2,2-dimethyl-4-phenyl-3-oxazoline N-oxide A solution of 70.2 g of 5-[p-(dimethylamino)-phenyl]-2,2-dimethyl-4-phenyl-3-oxazoline in 300 ml of glacial acetic acid was added while stirring to a mixture, cooled to 0° C., of 30 ml of acetic anhydride and 90 m. of 30% hydrogen peroxide. The mixture was then stirred at room temperature for an additional 2.5 hours, treated while cooling with sodium hydroxide (342 g of sodium hydroxide in 2 liters of water) and sufficient sodium carbonate was added until carbon dioxide no longer evolved. Then, the mixture was evaporated almost to dryness on a rotary evaporator in a water-jet vacuum at 60° C., and the residue was extracted with 2.5 liters of dichloromethane. The dichloromethane solution was dried over sodium sulfate, filtered and evaporated in a water-jet vacuum. The residue was chromatographed on silica gel, the elution being carried out firstly with acetone and subsequently with methanol. The fractions containing the product were combined and largely freed from solvent in a water-jet vacuum. There were thus obtained 52 g of a hygroscopic oil from which a part of the water was removed at room temperature and 0.1 Torr (4 hours). Crystallization was then carried out twice from acetone, the solution being decolorized with active carbon. The crystalline product was dried for 16 hours at 70° C. and 0.1 Torr, and there were obtained 40.8 g of 5-[p-(dimethylamino)phenyl]-2,2-dimethyl-4-phenyl-3-oxazoline N-oxide in the form of hygroscopic white crystals which decomposed during the melting from 130° C.

EXAMPLE 9

Preparation of
5-[(p-dimethylamino)-phenyl]-2,2-dimethyl-4-phenyl-3-oxazoline 1.275 kg of 4'-(dimethylamino)benzoin and 7.5 liters of acetone were warmed to 45° C. To the resulting suspension were added dropwise while stirring in the course of 5 hours under an argon atmosphere a solution of 1.140 kg of ammonium acetate in 6.25 liters of methanol and simultaneously 2.10 liters of triethylamine. The mixture was subsequently stirred at 45° C. for an additional 17 hours. The mixture was then cooled to room temperature and added while stirring to a mixture of 20 liters of ice, 10 liters of ethanol, 6 liters of formic acid and 10 liters of water. The resulting mixture was stirred for an additional 15 minutes, a substance separating out. This substance was removed by filtration under suction, washed with 5 liters of water and with a mixture of 2.5 liters of water and 2.5 liters of ethanol and then dried for 4 hours at 60° C. in a water-jet vacuum. There was thus obtained crude 5-[(p-dimethylamino)-phenyl]-2,2-dimethyl-4-phenyl-3-oxazoline which was purified as described in Example 1.

The 4'-(dimethylamino)benzoin used as the starting material can be prepared as follows:

1.061 kg of benzaldehyde and 1.492 kg of 4-(dimethylamino)benzaldehyde were dissolved together in 2.00 liters of dichloromethane and washed with a solution of 0.300 kg of sodium carbonate in 1.50 liters of water. The organic phase was separated and the dichloromethane was removed by distillation at 13 Torr and a bath temperature of 50° C. A yellow oil was obtained which was heated to reflux for 5 hours while stirring with 4.00 liters of ethanol, 0.300 kg of potassium cyanide and 2.00 liters of water. A finely crystalline white precipitate began to separate out after about 2 hours. The mixture was left to react for an additional 3 hours in the manner just described. After cooling, the mixture was suction filtered over a porcelain suction filter, and the residue was washed with a mixture of 3.00 liters of ethanol and 3.00 liters of water and subsequently with an additional 6.00 liters of water. The substance was dried for 24 hours at 13 Torr and 60° C. The thus-obtained 4-(dimethylamino)benzoin melted at 164°–165° C.

1.580 kg of 4-(dimethylamino)benzoin were dissolved in 3.00 liters of hydrochloric acid (about 37%). Hydrogen chloride gas was conducted into this solution for 10–20 minutes. The thus-obtained solution was left to stand for 48 hours at room temperature, about 2.00 liters of hydrochloric acid were removed by distillation at 13 Torr and 60° C., the still liquid residue was poured into 5.00 liters of ice/water with vigorous stirring and the mixture was adjusted to a pH of approximately 11 with 2.50 liters of sodium hydroxide (28%) while cooling. The precipitate which formed was dissolved in 15.00–18.00 liters of dichloromethane. The organic phase was separated, dried over sodium sulfate and concentrated to about 3800 ml, 4'-(dimethylamino)benzoin beginning to separate out. After cooling, the crystalline product, which was present in the yellow solution in the form of colorless needles, was removed by filtration under suction, washed absolute with 3.00 liters of ethanol and 1.50 liters of diethyl ether and dried for 5 hours at 13 Torr and 70° C. The product melted at 162°–164° C.

EXAMPLE 10

Preparation of
4-(o-chlorophenyl)-5-[p-(dimethylamino)phenyl]-2,2-dimethyl-3-oxazoline According to the procedure described in Example 1, from 30 g of 3-(o-chlorophenyl)-2,2-dimethyl-2H-azirine and 24 g of p-(dimethylamino)benzaldehyde there was obtained 4-(o-chlorophenyl)-5-[p-(dimethylamino)-phenyl]-2,2-dimethyl-3-oxazoline which melted at 72.5°–73.5° C. after drying for 4 hours at 35° C. and 13 Torr.

EXAMPLE 11

Preparation of
4-(m-chlorophenyl)-5-[p-(dimethylamino)phenyl]-2,2-dimethyl-3-oxazoline 3 g of 3-(m-chlorophenyl)-2,2-dimethyl-2H-azirine and 2.4 g of p-(dimethylamino)benzaldehyde were exposed to light for 2 hours in 350 ml of 1,4-dioxane (with the light source described in Example 2). After removing the solvent in a water-jet vacuum, the residue was chromatographed twice on aluminum oxide (neutral, activity 1), the elution was carried out in both cases with n-hexane/ether (9:1). Crystallization from n-hexane gave 4-(m-chlorophenyl)-5-[p-(dimethylamino)phenyl-2,2-dimethyl-3-oxazoline which melted at 96°–97° C. after drying for 5 hours at 60° C. and 13 Torr.

EXAMPLE 12

Preparation of
5-[p-(dimethylamino)phenyl]-2,2-dimethyl-4-(o-tolyl)-3-oxazoline 3.3 g of 2,2-dimethyl-3-(o-tolyl)-2H-azirine and 2.5 g of p-(dimethylamino)benzaldehyde were exposed to light for 2 hours in 290 ml of 1,4-dioxane (with the light source described in Example 2). After removing the solvent in a water-jet vacuum, the residue was chromatographed on aluminum oxide (neutral, activity 1), the elution was carried out with n-heptane/ether (9:1). Crystallization from ethanol/water gave 5-[p-(dimethylamino)phenyl]-2,2-dimethyl-4-(o-tolyl)-3-oxazoline which melted at 89°–90° C. after drying for 16 hours at 30° C. and 13 Torr.

EXAMPLE 13

Preparation of
5-[4-(dimethylamino)-3,5-xylyl]-2,2-dimethyl-4-phenyl-3-oxazoline 2.6 g of 2,2-dimethyl-3-phenyl-2H-azirine and 2,5 g of 3,5-dimethyl-4-(dimethylamino)benzaldehyde were exposed to light for 2 hours in 300 ml of 1,4-dioxane (with the light source described in Example 2). After purification as described in Example 12 and crystallization from n-pentane, there was obtained 5-[4(dimethylamino)-3,5-xylyl]-2,2-dimethyl-4-phenyl-3-oxazoline which melted at 91°–92° C. after drying for 2 hours at 50° C. and 13 Torr.

EXAMPLE 14

Preparation of
5-[4-(dimethylamino)-2,6-xylyl]-2,2-dimethyl-4-phenyl-3-oxazoline 2.25 g of 2,2-dimethyl-3-phenyl-2H-azirine and 2 g of 2,6-dimethyl-4-(dimethylamino)benzaldehyde were exposed to light for 3 hours in 350 ml of 1,4-dioxane (with the light source described in Example 2). After purification as described in Example 11 and crystallization from n-pentane, there was obtained 5-[4-(dimethylamino)-2,6-xylyl]-2,2-dimethyl-4-phenyl-3-oxazoline which melted at 105° C. after drying for 4 hours at 60° C. and 13 Torr.

EXAMPLE 15

Preparation of 5-(p-aminophenyl)-2,2-dimethyl-4-phenyl-3-oxazoline 48 g of 2,2-dimethyl-3-phenyl-2H-azirine and 18.5 g of p-aminobenzaldehyde were exposed to light for 2 hours in 6 liters of 1,4-dioxane in the manner described in Example 1. The solvent was then removed in a water-jet vacuum and the oily residue was chromatographed on silica gel, the elution was carried out with dichloromethane. The thus-obtained crude product (60 g) was stirred in ethanol for 2 hours at room temperature together with 1.8 g of sodium borohydride. The mixture was then diluted with water and extracted with dichloromethane. The crude product obtained after drying and evaporation of the organic phase was purified by pressure chromatography (6 bar) on silica gel with dichloromethane/ether (3:1), whereby there was obtained a product which, after 2-fold recrystallization from ethanol, yielded 5-(p-aminophenyl)-2,2-dimethyl-4-phenyl-3-oxazoline having a melting point of 162°–163° C. after drying for 4 hours 90° C. and 13 Torr.

The p-aminobenzaldehyde used as the starting material polymerizes readily and is only stable in dilute solutions for a short time. It can be prepared as follows:

50 g of polymeric p-aminobenzaldehyde were depolymerized by heating on a steam-bath for 2 hours in hydrochloric acid (300 g of concentrated hydrochloric acid and 1700 ml of water). After cooling, the resulting mixture was neutralized with a mixture of 135 g of sodium hydroxide, 2 liters of water and 4 kg of ice and extracted twice with 3 liters (a total of 6 liters) of ether. The organic phase was then dried over magnesium sulfate, filtered and the ether was removed from the mixture by distillation while 1,4-dioxane was repeatedly added to attain the aforementioned total volume of 6 liters. The content of p-dimethylaminobenzaldehyde was determined by evaporating an aliquot of the solution to dryness and weighing the residue.

EXAMPLE A

Tablets for oral administration can contain the following ingredients:

| | |
|---|---|
| Active substance [e.g. 5-[p-(dimethylamino)-phenyl]-2,2-dimethyl-4-phenyl-3-oxazoline] | 500.00 mg |
| Microcrystalline cellulose | 44.75 |
| Sodium carboxymethylstarch | 40.00 |
| Polyvinylpyrrolidone | 12.00 |
| Dioctyl sodium sulfosuccinate | 0.25 |
| Magnesium stearate | 3.00 |
| | 600.00 mg |

We claim:

1. A compound of the formula

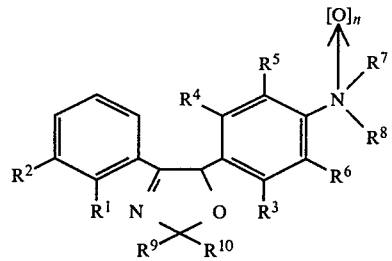

wherein $R^1$ and $R^2$, independently, are hydrogen, halogen or lower alkyl; $R^3$, $R^4$, $R^5$, $R^6$ and $R^7$, independently, are hydrogen or $C_{1-3}$ alkyl; $R^8$ is hydrogen, lower alkyl or formyl; $R^9$ and $R^{10}$, independently, are methyl or trifluoromethyl; and n is 0 or, when both $R^7$ and $R^8$ are lower alkyl, n is 0 or 1.

2. A compound in accordance with claim 1, wherein each of $R^1$–$R^6$ is hydrogen and $R^7$ is $C_{1-3}$ alkyl.

3. A compound in accordance with claim 1, wherein each of $R^9$ and $R^{10}$ is methyl.

4. A compound in accordance with claim 1, wherein n is 0.

5. A compound in accordance with claims 1, 2, 3 or 4, wherein each of $R^7$ and $R^8$ is methyl.

6. A compound in accordance with claim 1, 5-[p-(dimethylamino)phenyl]-2,2-dimethyl-4-phenyl-3-oxazoline.

7. A compound in accordance with claim 1, selected from the group consisting of 5-[p-(diethylamino)-phenyl]-2,2-dimethyl-4-phenyl-3-oxazoline, 5-[p-(dipropylamino)phenyl]-2,2-dimethyl-4-phenyl-3-oxazoline, 5-[p-(methylamino)phenyl]-2,2-dimethyl-4-phenyl-3oxazoiline, 4'-(2,2-dimethyl-4-phenyl-3-oxazolin-4-yl)-N-methylformanilide, 5-[p-(dimethylamino)phenyl]-2,2-dimethyl-4-phenyl-3-oxazoline N-oxide, 4-(o-chlorophenyl)-5-[p-(dimethylamino)phenyl]-2,2-dimethyl-3-oxazoline, 4-(m-chlorophenyl)-5-[p-(dimethylamino)-phenyl]-2,2-dimethyl-3-oxazoline, 5-[p-(dimethylamino)-phenyl]-2,2-dimethyl-4-(o-tolyl)-3-oxazoline, 5-[4-(dimethylamino)-2,6-xylyl]-2,2-dimethyl-4-phenyl-3-oxazoline and 5-(p-aminophenyl)-2,2-dimethyl-4-phenyl-3-oxazoline.

* * * * *